US009005990B2

(12) United States Patent
Koch et al.

(10) Patent No.: US 9,005,990 B2
(45) Date of Patent: Apr. 14, 2015

(54) METHOD FOR PURIFICATION OF COLISTIN AND PURIFIED COLISTIN COMPONENTS (75) Inventors: Torben Koch, Copenhagen (DK); Carsten Overblle Petersen, Hvidovre (DK)

(73) Assignee: Xellia Pharmaceuticals APS (DK)

( * ) Notice: Subject to any disclaimer, the term of this patent is extended or adjusted under 35 U.S.C. 154(b) by 107 days.

(21) Appl. No.: 13/504,485

(22) PCT Filed: Sep. 29, 2010

(86) PCT No.: PCT/EP2010/064472
§ 371 (c)(1),
(2), (4) Date: Apr. 27, 2012

(87) PCT Pub. No.: WO2011/051070
PCT Pub. Date: May 5, 2011

(65) Prior Publication Data
US 2012/0208981 A1  Aug. 16, 2012

Related U.S. Application Data (60) Provisional application No. 61/256,344, filed on Oct. 30, 2009.

(51) Int. Cl.
G01N 1/00 (2006.01)
G01N 1/18 (2006.01)
G01N 30/02 (2006.01)
B01D 11/00 (2006.01)
C07K 7/62 (2006.01)

(52) U.S. Cl.
CPC .................................. C07K 7/62 (2013.01)

(58) Field of Classification Search
CPC ........ A61K 38/00; A61K 38/14; A61K 45/00; A61K 47/48415; C07K 7/62
See application file for complete search history.

(56) References Cited

U.S. PATENT DOCUMENTS

2005/0133452 A1* 6/2005 Winkel Pettersson et al. ................ 210/656
2006/0175258 A1* 8/2006 Johansson et al. ............ 210/656
2007/0269899 A1* 11/2007 Shimbo et al. ................. 436/89

FOREIGN PATENT DOCUMENTS

| CN | 101525377 | 9/2009 | |
|---|---|---|---|
| WO | WO 98/20836 | * 5/1998 | |
| WO | WO 2007/071767 | * 6/2007 | C12N 9/64 |

OTHER PUBLICATIONS

Li J, et al, "Colistin: the re-emerging antibiotic for multidrug-resistant Gram-negative bacterial infections", Lancet Infectious Diseases, Elsevier Ltd, vol. 6, No. 9, Sep. 1, 2006, pp. 589-601.
Gmur D J, et al, "Determination of polymyxin E1 in rat plasma by high-performance liquid chromatography", J. Chromatography B: Biomedical Sciences & Applications, vol. 789, No. 2, Jun. 15, 2003, pp. 365-372.

(Continued)

Primary Examiner — Ja'Na Hines
(74) Attorney, Agent, or Firm — Cantor Colburn LLP (57) ABSTRACT The present invention concerns a method of purifying colistin using reverse phase chromatography, wherein loading a column with colistin base in acetic acid and high ethanol concentration and eluting with low ethanol concentration is performed.

11 Claims, 3 Drawing Sheets (56) References Cited

OTHER PUBLICATIONS

Decrescenzo, Henriksen et al, "Polymyxin E production by P. amylolyticus", Letters in Applied Microbiology, Oxford, vol. 45, Jan. 1, 2007, pp. 491-295.

Elverdam, Ingelise; "Isolation and Characterization of Three New Polymyxins in Polymyxins B and E by High-performance Liquid Chromatography"; Journal of Chromatography; 218; pp. 653-661; (1981).

Falagas et al.; "Toxicity of Polymyxins: a Systematic Review of the Evidence From Old and Recent Studies"; Critical Care; 10(1); pp. 1-13; (2006).

Michalopoulos et al.; "Colistin and Polymyxin B in Critical Care"; Crit Care Clin; 24; pp. 377-391; (2008).

Suzuki et al.; "Studies on the Chemical Structure of Colistin, III. Enzymatic Hydrolysis of Colistin A"; The Journal of Biochemistry; 54(5); pp. 412-418; (1963).

\* cited by examiner

METHOD FOR PURIFICATION OF COLISTIN AND PURIFIED COLISTIN COMPONENTS

FIELD OF INVENTION

The present invention relates to a process for purifying antibiotics.

BACKGROUND

Increasing multidrug resistance in Gram-negative bacteria, in particular *Pseudomonas aeruginosa, Acinetobacter baumannii*, and *Klebsiella pneumoniae*, presents a critical problem. Limited therapeutic options have forced infectious disease clinicians and microbiologists to reappraise the clinical application of colistin (also called polymyxin E), a polymyxin antibiotic that is similar to, but not identical with polymyxin B. Colistin may have distinct advantages over polymyxin B because of its wider therapeutic index.

Figure 1:
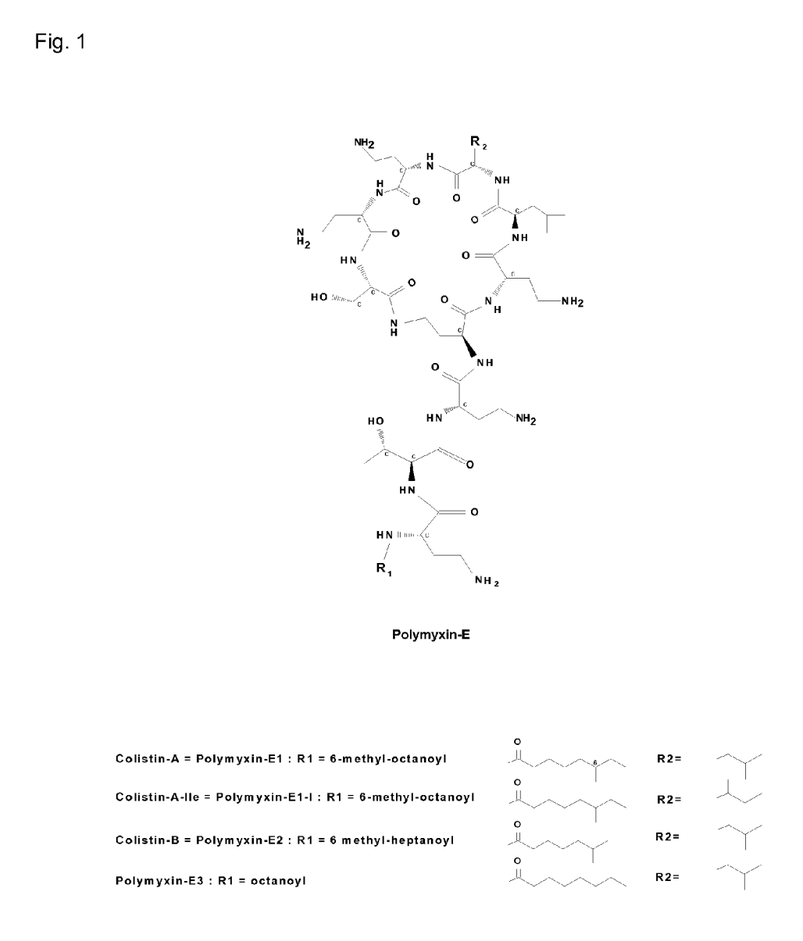

Colistin was first isolated in 1947 from *Bacillus polymyxa* var. *colistinus* and consists of a mixture of polypeptides produced by fermentation. Main components are polymyxin $E_1$, $E_2$, $E_3$ and $E_1$-Ile (FIG. 1).

Commercially, colistin appears as colistin sulfate, which is used orally for bowel decontamination and topically as a powder for skin infections, and as colistimethate sodium, which is used parenterally and by inhalation. Colistimethate sodium has been found to be less toxic and to have fewer undesirable side effects than colistin, but is also less potent. (See; Critical Care 2006, 10:R27 (doi:10.1186/cc3995) by Falagas and Kasiokou).

Colistin sulfate is often formulated in ointments, otic suspensions and otic and ophthalmic solutions. Colistin sulphate is also administered orally as suspensions or tablets to treat intestinal infections, or to suppress colonic flora.

Colistimethate sodium is a semi synthetic pro-drug of colistin which may be used to treat *Pseudomonas aeruginosa* infections in cystic fibrosis patients and it has come into recent use for treating multidrug-resistant *Acinetobacter* infections. Colistimethate sodium has also been given intrathecally and intraventricularly in *Acinetobacter baumannii* and *Pseudomonas aeruginosa* meningitis/ventriculitis. Colistimethate sodium is readily hydrolysed to a variety of methanesulphonated derivatives in aqueous solution, and is very difficult to analyse.

Because colistin was introduced into clinical practice over 50 years ago, its properties were never documented as thoroughly as modern drugs are, e.g. with specific requirements related to pharmacology, toxicology, content of impurities, etc.

Figure 2:
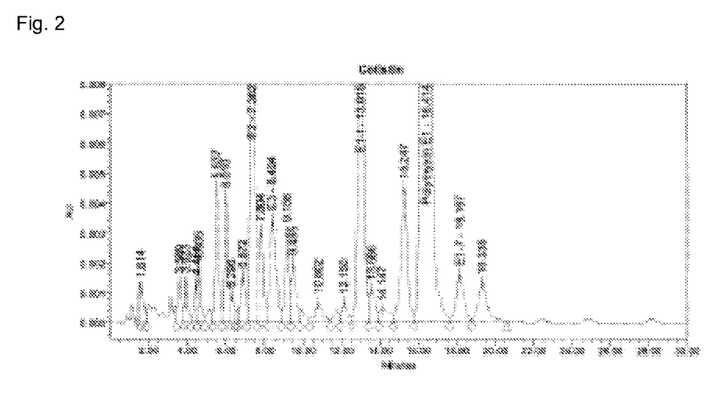

For this reason, commercially available colistin products contain, in addition to is main component polymyxin $E_1$, many related active and inactive substances/impurities, mostly stemming from the fermentation process. A typical HPLC chromatogram of colistin is shown in FIG. 2.

The main component of commercial colistin, polymyxin $E_1$, typically constitutes approx. 60% of the dry product. Some of the related substances in colistin products have been characterized (FIG. 1), but most impurities are still unknown. The minimum potency of colistin sulfate as specified by USP (United States Pharmacopoeia) is "not less than 500 μg/mg", but the specific antimicrobial activity of each component is largely unknown.

Even though the product has been used for more than 50 years, there is no standardised dosing of colistin and no detailed trials published on pharmacology or pharmacokinetics. The optimal dosing of colistin for most infections is therefore unknown. Likewise, the recommended "maximum" dose for each preparation is different. Each country has different generic preparations of colistin and the recommended dose will depend on the manufacturer.

Colistin sulfate and colistimethate sodium may both be given intravenously and as aerosols, but the dosing is complicated. Colistimethate sodium from some manufacturers is prescribed in international units, while same product from other manufacturers is prescribed in milligrams of colistin base. This complete absence of any regulation or standardisation of dose makes intravenous colistin dosing a nightmare for any physician.

The main toxicities described with intravenous treatment are nephrotoxicity (damage to the kidneys) and neurotoxicity (damage to the nerves), but this may reflect the very high doses given in earlier days, which were much higher than the doses currently recommended by any manufacturer and for which no adjustment was made for renal disease. The main toxicity described with aerosolised treatment is bronchospasm.

In the absence of supporting data, one may speculate that some of the toxicity of colistin may be ascribed to related substances and impurities present in the current commercial products. And furthermore, when synthesising the colistimethate pro-drug using "impure" colistin as starting material, each related substance and impurity will form basis for several methane sulphonate derivatives, thereby creating a very complex final product—where the toxicological properties of each individual substance are unknown.

Based on toxicological and pharmacological considerations above, one may see great advantages in using a "mono-component" variety of colistin for medicinal purposes. Such a mono-component colistin will contain a very high proportion of the main component polymyxin $E_1$ (>90%, compared to current 60%), with all major impurities identified and characterised.

A mono-component colistin offers several advantages:
1) Possibility of clarifying toxicological contributions of main component ($PE_1$), related substances and impurities
2) Product amenable to new and more precise pharmacological and pharmacokinetic investigations
3) Possibility of synthesising well-defined derivatives, e.g. colistimethate without creating a multitude of ill-defined substances
4) Possibility of developing better and more precise analytical methods both for colistin and colistimethate, simplifying regulatory procedures
5) Unambiguous dosing recommendation based on clear-cut pharmacological and toxicological data
6) Upgrade of colistin to a "modern" antibiotic, which is in great demand Since an industrially scaleable method for preparation of a mono-component colistin is not described in the patent literature or elsewhere in the public domain, it has been the goal of the inventor to develop a manufacturing process for such a product.

A second, longer term goal would be to subject the purified $PE_1$ to renewed studies of in vitro and in vivo effectiveness and to toxicological studies in order to compare with older studies of the polymyxin group. Such randomized and controlled trials are urgently needed to further clarify various issues regarding the effectiveness and safety of polymyxins (Crit Care Clin. 2008 April; 24(2):377-91, by Micholopoulos and Falagas).

SUMMARY OF INVENTION

The present invention concerns a method for purifying colistin components, and in particular the main component, polymyxin $E_1$.

The present invention relates to a method for producing a virtually pure preparation of the main component of colistin, polymyxin $E_1$ (90-98% purity), termed colistin mono-component.

The method is a simple, chromatographic method employing solvents of low toxicity. The method involves reverse phase (RP) chromatography, which allow purification of Polymyxin $E_1$ to a purity of more than 90%, followed by hydrophobic interaction chromatography (HIC).

The method is characterized by
loading of RP column with colistin base in acetic acid and high (4 M) ethanol concentration
eluting with low (1.6-2 M) ethanol concentration.

Surprisingly, the method can be used to efficiently separate Polymyxin $E_1$ from the other main colistin components.

The work involving identification of a suitable RP-material was performed in laboratory scale on 10×250 mm steel columns.

Merck LiChrospher 60 RP-select B, 15 μm (C8) turned out to be a suitable resin for purification of $PE_1$ from colistin base in laboratory scale, and the lab method was scaled up from one gram to fifty gram level on a 50×850 mm steel column.

A method was developed, whereby colistin base was dissolved in 24% (4 M) ethanol and 0.1M acetic acid and separated into polymyxin E fractions. The main component, $PE_1$ was isolated with a typical recovery of 60% and a relative chromatographic purity of 94-98%.

In the European Pharmacopoeia (EP) the potency of a batch/lot of colistin sulfate is defined as % content of the sum of the polymyxin factors $PE_1$, $PE_2$, $PE_3$, $PE_1$-Ile and $PE_1$-7MOA, determined by HPLC on "as is" basis. The total potency of these factors should constitute not less than 77.0%. Furthermore, EP states maximum limits (NMT; not more than) of specific factors as: $PE_1$-Ile (NMT 10%), $PE_1$-7MOA (NMT 10%), $PE_3$ (NMT 10%), and Major impurity NMT 4%.

By use of the described purification method, the final product has a typical composition as follows: $PE_1$ (94-98%), $PE_2$ (0-0.1), $PE_3$ (0.0), $PE_1$-Ile (0.2-1.0%), $PE_1$-7MOA (0.5-2.0%), and total remaining impurities 0.5-2.0%.

BRIEF DESCRIPTION OF FIGURES

FIG. 1. Molecular structure of the main component of colistin sulfate, polymyxin $E_1$ sulfate and related substances FIG. 2. HPLC chromatogram of colistin Ph. Eur. chemical reference substance FIG. 3. The graphs are illustrating the relative chromatographic purity as function of fraction number during purification of colistin base; f1-E1 and f2-E1 in the graph are collectively referred to as $f_1$ in the descriptive part of the application; eE1 is equivalent to $e_1/e_2$, eeE1 is equivalent to $e_3$, while eee . . . is the sum of minor unknown impurities FIG. 4. The graphs are illustrating the peak areas of the various components as function of fraction number during purification of colistin base; f1-E1 and f2-E1 in the graph are collectively referred to as $f_1$ in the descriptive part of the application; eE1 is equivalent to $e_1/e_2$, eeE1 is equivalent to $e_3$, while eee . . . is the sum of minor unknown impurities FIG. 5. HPLC chromatogram of colistin mono-component ($PE_1$) with main impurities

DETAILED DESCRIPTION OF INVENTION

"Colistin" is meant to cover any mixture of antibiotic peptide components where the main component is Polymyxin $E_1$ or salts thereof "Polymyxin $E_1$" is meant to embrace the compound formerly designated Colistin A,
as well as
the compound designated 7722-44-3 by Chemical Abstracts,
as well as
N2-(6-Methyl-1-oxooctyl)-L-2,4-diaminobutanoyl-L-threonyl-L-2,4-diaminobutanoyl-L-2,4-diaminobutanoyl-L-2,4-diaminobutanoyl-D-leucyl-L-leucyl-L-2,4-diaminobutanoyl-L-2,4-diaminobutanoyl-L-threonine cyclic (10-4)-peptide,
As well as
Colistin IV.

"Colistin base" is meant to embrace any colistin comprising 30-70% Polymyxin $E_1$.

"Colistin sulfate" is meant to embrace any sulphate salt of colistin

"Colistimethate" is meant to embrace any methane sulfonated derivative of colistin A "composition" is any mixture comprising more than two different compounds, for example a mixture of two active pharmaceutical ingredients, or a mixture of an active pharmaceutical ingredient and one or more pharmaceutical excipients.

The term "component" or "components" used in this application is referring to a specific compound in a composition. Accordingly, "Minor components" are compounds found in relatively small amounts in a composition.

A "pharmaceutical composition" is any composition suitable for use in vivo. Such compositions can thus be administered cutaneously, subcutaneously, intravenously, parenterally, orally etc.

"Separation" is any method wherein a desired compound is resolved from another compound (analytically or preparatively).

"Purification" is any separation method by which the concentration of a desired compound is increased.

"Chromatography" is any purification technique involving a stationary phase and a mobile phase.

"A stationary phase" is any surface comprising ligands capable of retaining compounds.

"Ligands" are moieties of the stationary phase, at which the binding of compounds occurs.

"A mobile phase" is any fluid, solvent, liquid or mixture that can percolate through or along the stationary phase in a definite direction.

"Reverse phase chromatography" is any chromatography in which the more polar or charged components are eluted before the less polar ones.

"Hydrophobic interaction chromatography" is any chromatography based on interaction between non-polar ligands of stationary phase and non-polar compounds or non-polar part of compounds "High ethanol concentration" means ethanol concentrations higher than, or equal to 20% of volume, typically 20%-30%

"Low ethanol concentration" means ethanol concentrations lower than 20% of volume, typically 10%-15%

"% v/v" means volume percentage

Commercial colistin base is a mixture of many closely related decapeptide-fatty acid amides, including polymyxin $E_1$, polymyxin $E_2$, polymyxin $E_3$ and polymyxin $E_1$-isoleucin (FIG. 1).

The ambition to isolate the main component polymyxin $E_1$ ($PE_1$) from colistin base led to an investigation of whether or not a reverse phase (RP) HPLC method would be suitable for isolation of, and to obtain $PE_1$ of high relative chromatographic purity (>90%).

Literature provides only few RP separation methods, and main organic solvents used are acetonitrile and methanol. These solvents are toxic and should be avoided in pilot and large scale production. However, a microgram level C18-HPLC separation trial with colistin sulfate employing an ethanol gradient from 0 to 60% indicated, quite surprisingly that it might be possible to use the relatively non-toxic solvent ethanol for an industrially useful purification method for polymyxin $E_1$.

The starting material, colistin base, is produced by fermentation and purification, and is an intermediate in the production of the bulk substance colistin sulfate. The starting material contains approx. 60% $PE_1$, varying with a few percent between batches. The original goal was to achieve a relative chromatographic purity of polymyxin $E_1$ sulfate of >90%. With this as target, a range of column materials was screened with elution systems based on ethanol.

Polymyxin $E_1$ (FIG. 1) has ionic detergent character with a polar decapeptide part and a non-polar fatty acid part. The molecule consists of a cyclic heptapeptide attached to a 6-methyl-octane acylated linear tripeptide. As the molecule contains 6 moieties of 1,4-diaminobutyric acid (DAB), of which one participates in three peptide bonds, there are 5 primary amino groups in equilibrium with their corresponding ammonia ($NH_4^+$) groups, constituting the strong polar part of the molecule.

The molecular interaction between the RP-resin and the molecule is anticipated to take place at the fatty acid moiety and the non-polar regions of the peptide part.

For monitoring the HPLC-fractions and -pools, an analytical HPLC-method was developed based on a standard method. The improved method revealed a small amount related components ($f_1$, $e_1$, $e_2$) underneath the $PE_1$ main peak that were invisible when using the conventional HPLC method.

Experimental

Preparative HPLC

10×250 Column:
For screening of column materials in milligram scale, a steel column 10×250 mm was used. The column was filled with the various tested resins suspended in 96% ethanol.

50×830 Column:
For preparative purification in gram scale, a 50×850 mm steel column was used as described below. The selected column material, approx. 1 kg Merck LiChrosphere 60 RP select B (15 µm), was suspended in 96% ethanol and filled onto the column. The top flange was attached and the piston pushed upwards at 50 bar until all excess ethanol was removed. The column was tested by applying 1 ml of a 0.1 mg/ml potassium iodide solution, and absorption was measured at 227 nm, AUFS=0.05 and flow 55.5 ml/min. The recorded peak was a narrow Gauss-curve with satisfactory symmetry.

The preparative HPLC system consisted of:
Columns: 10×250 mm stainless steel Merck column and a 50×850 mm stainless steel column with a dynamic axial compression produced by Dan Process A/S
Pumps: Waters Delta Prep 4000 with a flow interval of 0.5-150 ml/min, with 4 different solvent ports with a mix-valve on the low pressure side
Detector: Waters 486 Tunable Absorbance Detector
Integrator: Merck-Hitachi D-2000 Chomato-Integrator
Fraction collector: Waters Fraction Collector The absorbance of the eluent was detected at 230 nm, where there is a cut-off for acetic acid. At shorter wavelengths, the eluent showed too much interference. Fractions in milligram scale were collected in 25 ml test tubes, while fractions in gram scale were collected in 250 ml Bluecap bottles.

For regeneration of the 10×250 mm and 50×850 mm columns after each HPLC-run, a mix containing 24% ethanol and 50% 1,2-propylene glycol in 0.1M $CH_3COOH$ was used. Occasionally, high counter pressure was observed with the 50×850 mm column, which was then re-packed or flushed with 96% ethanol until pressure became normal.

Analytical HPLC:
Employed column was Novapak 4.6×150, 4 µm, C18 with acetonitrile as mobile phase. The concentration of the $CH_3CN$-solution was increased from 21% (after 10 minutes isocratic run) to 30% during a 5 min. time interval. The columns were not thermostated, but run at ambient temperature (23±2° C.).

The analytical HPLC-system consisted of:
Columns: Waters Novapak 4.6×150, 4µ C18 and equivalent 4.6×250 column
Pumps: 2 psc. Waters 510 with Waters Pump Control Module
Detector: Waters 490 E Programmable Multi-wavelength Detector
Fraction collector: Waters 717 plus Autosampler
The system was controlled by Waters software Millenium.

Overview of Tested Resins:
1) Merck No. 9303 LiChroprep RP-18, 25-40 µm, batch: L 275703 614.
2) Merck No. 9324 LiChroprep RP-8, 25-40 µm, batch: L 240124 541.
3) Merck No. 11023 LiChrospher 60 RP-select B, 15 µm, (C8), batch: L 139923 633.
4) Merck No. 150385 Hibar Fertigsäule RT LiChrospher, RP-18, 15 µm, Cat. 50014.
5) Eka Nobel Kromasil-100 Å, C8, 16 µm, batch: DT0026.
6) ToosoHaas Amberchrom CG 71 S, 35 µm, Lot No. 23770319.
7) ToosoHaas No. 22227 Toyopearl MD-P Ether, 35 µm, weakly hydrofobic
8) ToosoHaas No. 22225 Toyopearl MD-P Butyl, 35 µm, strongly hydrofobic Chemicals for the 10×250 Column Trials:
Colistin sulfate, batch: A4660314, Axellia ApS, Copenhagen DK
Colistin base, batch: A1551701, Axellia ApS, Copenhagen, DK
Ethanol, 96%, "Danisco Distillers", Danisco A/S
Methanol, Merck LiChrosolv no. 6018
Dimethylsulfoxide, Merck Uvasol No. 2950
1,2-Propandiol reinst, Merck no. 7478
2-Propanol, LiChrosolv gradient grade, Merck No. 1040
Acetic Acid, 100% G.R. Merck No. 63
1-Methylpyrrolidon-(2) z.s., Merck No. 806072
Triethylamine, Pierce No. 25108
Tetrahydrofurane, Fluka No. 87367
Ammonium acetate p.a., Merck No. 1116
Ammonium sulfate p.a., Merck No. 1217
Sulphuric Acid 98% p.a.
Sodium hydroxide pellets, GR, Merck No. 6498
Mili-Q-water, Purification lab., R&D, FCD, Axellia ApS, Copenhagen, DK
Millipore, type HV membrane filter, 0.45 µm.

Chemicals for the 50×825 Column Trials:
Ethanol 96% and 99.9% from Danisco Distillers, Danisco A/S
Acetic Acid, 100% G.R. Merck No. 63
Sodium hydroxide pellets, GR, Merck No. 6498
NaOH, 27% Production dept.
Potassium hydroxide, USP XIX, Ferak Berlin No. 20907
  10×250 Column Trials:
  The following chromatographic resins proved unsuitable for the separation task either due to strong binding to resin, pronounced tailing, low chromatographic purity or low recovery: ToosoHaas Amberchrom CG 71 S; ToosoHaas Toyopearl MD-P Ether, 35 µm, ToosoHaas Toyopearl MD-P Butyl, 35 µm; Merck LiChroprep RP-8, 25-40 µm; Merck Hibar Fertigsäule RT LiChrospher, RP-18, 15 µm; Eka Nobel Kromasil-100 Å, C8, 16 µm For the first 10×250 column trials with Lichroprep C18, 25-40 µm with an ethanol gradient from 0% to 60% during 60 min. at pH~3.5 (50 mM HAc) with applied 11 mg colistin sulfate, a relative chromatographic purity (RCP) of approx. 90% with good yields was obtained. However, when attempting to reduce the ethanol concentration by applying a 10-25% ethanol gradient during 45 min. at same conditions, no separation and a pronounced tailing was observed.

Similar trials with 5 mM $NH_4HSO_4$ at pH=2.5 resulted in complete binding of compounds on the column. This, and similar experiments strongly indicated that colistin base, rather than colistin sulfate should be used for $PE_1$ purification with the selected conditions.

If 1,2-propylene glycol (1,2-PG) was added as substitute for part of the ethanol, e.g. at a concentration level of 24% ethanol and 20% 1,2-PG, and the acetic acid level (pH=3) was increased to approx. 1%, this gave, surprisingly a $PE_1$ product with an RCP of approx. 90% with 70% yield.

Based on these initial experiments, it was concluded that acetic acid had a positive influence on the compound equilibrium between resin (LiChroprep C18) and eluent, and that one should rather use colistin base dissolved in diluted acetic acid instead of colistin sulfate. However, the use of a 1,2-propylene glycol/ethanol mix resulted in a pronounced pressure drop with this column material, and this particular resin and solvent mix were therefore considered unsuitable for scale-up.

It became obvious that not only the fatty acid moiety and non-polar amino acids were involved in column binding, but that also amino- and ammonium groups were involved.

Above experiments gave some surprising results, e.g. that a) the EHS-friendly solvent ethanol was useful as eluent for reverse phase (RP) HPLC separation of colistin, and that b) separation should be performed with colistin base in the presence of acetic acid instead of using colistin sulfate for further purification. Although the resin LiChroprep C18 exhibited promising separation properties, it did not prove suitable for scale-up.

The list of commercially available chromatographic media is extensive, but by thorough screening and selection we succeeded in identifying a suitable candidate from Merck, namely LiChrospher 60 RP-select B 15 µm (C8).

Use of linear gradients from 5 to 24% ethanol in 0.1 M acetic acid gave promising separations with little tailing. Gradients from 5 to 15% ethanol in 0.1 M acetic acid (pH=3) worked well, but with an RCP of only 85-90% $PE_1$ and with low yields.

A major breakthrough came when a reversed ethanol gradient was tried out (i.e. application at high concentration and elution at lower concentration of ethanol). The first trials with the following parameters turned out to give a pool with 90-95% $PE_1$ and approx. 70% yield:
Equilibration: 5% ethanol in 0.1 M acetic acid
Application: 110 mg colistin base dissolved in 4 ml 30% ethanol in 0.1 M acetic acid
Eluent: 15% ethanol in 0.1 M acetic acid at a temperature of 60° C.
Temperature: 40° C.
Eluent flow: 2.22 ml/min.

The higher temperature was selected in order to reach equilibrium of the colistin components between solid phase and eluent faster, but experiments showed that the higher temperature did not have any marked influence on the results. The temperatures of both column oven and eluent phase were therefore reduced from 40°/60° to 35°/50° without any significant change of pool purity and yield. Finally, a 5 to 15% ethanol gradient in 0.1 M acetic acid was run at 30°/40° with good results, confirming that the reversed gradient was actually responsible for the large positive change in relative chromatographic purity, yield and tailing profile.

It should be noted that a modified, analytical HPLC method was implemented during the development work, and that this new method revealed some related substances, $f_1$ and $e_1/e_2$, that were previously masked by the main $E_1$ peak.

The related substance $f_1$ elute at the front of the $PE_1$ peak, while the substances $e_1/e_2$ elute as a double peak with two more or less split maxima at the tail of the $PE_1$ peak. These two substances are particularly difficult to separate from $PE_1$ and constitute a purification challenge in future optimization of the preparative HPLC method. See in particular FIG. 3 and FIG. 4, where separation of $PE_1$ and related substances are illustrated with diagrams showing the distribution of components as function of HPLC fraction.

Figure 3:
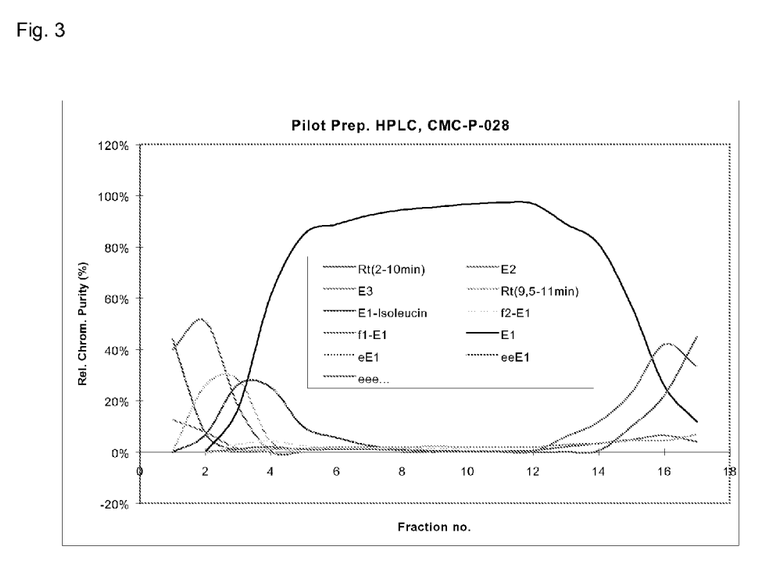
Figure 4:
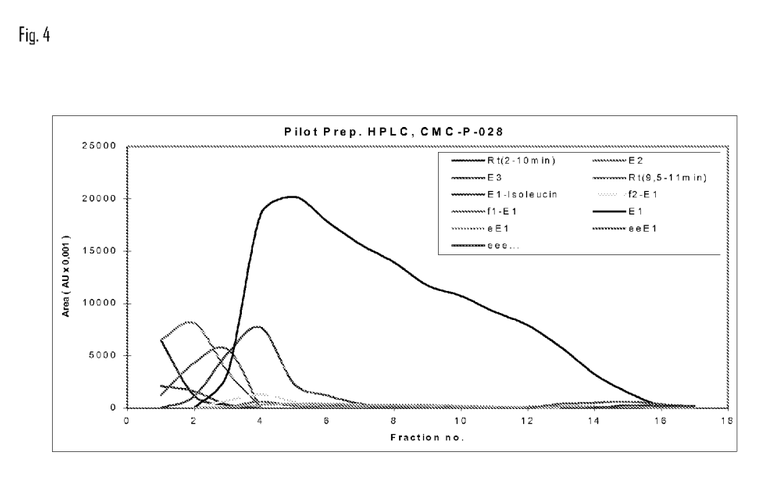
Figure 5:
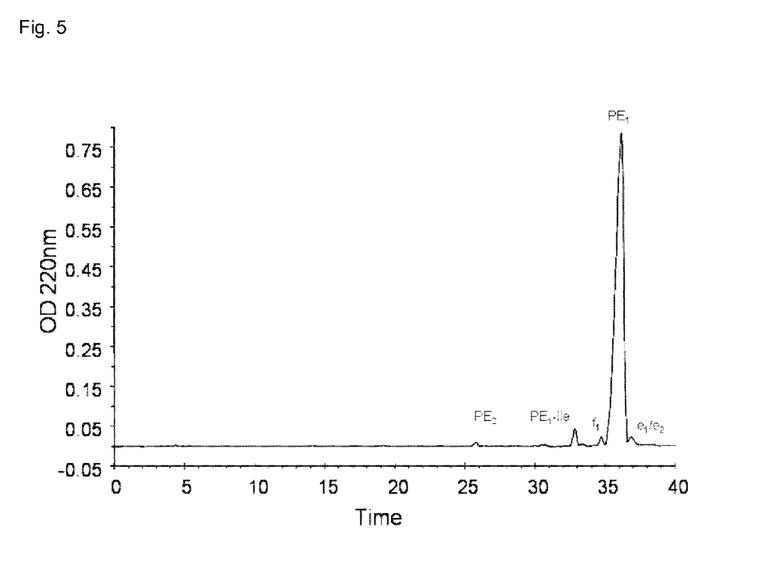

In FIG. 3 the relative chromatographic purity of polymyxin $E_1$ is compared to related substances as function of fraction number. The related substances that are most difficult to separate from $PE_1$ are $e_1/e_2$, while $E_1$-isoleucin, $f_1$ and $e_3$ (eluting after $e_1/e_2$) are easier to remove. FIG. 4 is showing the results from a yield perspective, where integration of the component peaks are plotted as function of fraction numbers. The main pool is typically spanning fractions 7 to 12, but purity may be increased by narrowing the fraction selection.

EXAMPLES

Procedures for Purification of Polymuxin E1 from Colistin Base

Example 1

RP-HPLC Purification; Miniprep Scale

Equipment: Steel column 10×250 mm (ø=10 mm)
  Waters Delta Prep 4000 Prep. Chrom. System
  Waters 4000 System Controller
  Waters 486 Tunable Absorbance Detector
  Waters Fraction Collector
  Merck Hitachi D-2000 Chromato-Integrator
Resin: LiChrospher 60 RP-select B Merck No: 11023.
Flow: 2.22 ml/min. (Scaled up to 300×700 mm~2 L/min.)
λ: 230 nm
AUFS: 2 (detector sensitivity~lowest level).
A-buffer: 12% Ethanol (96%) in 0.10 M $CH_3COOH$ in Mili-Q-water
Application sol.: Colistin base, 600 mg~0.5 mmol dissolved in 15 ml 24% Ethanol (from 96%) in 0.10 M $CH_3COOH$ by addition of 5 acid equivalents of $CH_3COOH$~2.5 mmol~0.15 ml 100% $CH_3COOH$ (17M); adjusted with 2 M NaOH to pH=7.5; solution is membrane filtered (0.45 μm)

1) Equilibration of column: Equilibrated with A-buffer
2) Application: The colistin acetate solution (40 mg/ml) is applied at 2.22 ml/min, followed by 1 ml A-buffer through the feeding tube
3) Elution: The column is eluted immediately with A-buffer and effluent is collected in 1 ml fractions~2.22 ml
4) Wash of column: 5 ml 96% ethanol is applied, followed by A-buffer until absorption has decreased to zero level
5) HPLC analysis: Samples are diluted until area of $E_1$ reaches $20\text{-}30 \times 10^6$ AU; high colistin standard typically reaches $20 \times 10^6$ AU; samples are analyzed by use of Colistin NovaS (30 min. run).

Example 2

RP-HPLC Purification; Pilot Scale

Equipment: Steel column 50×830 mm (ø=50 mm), "Danprocess"
Waters Delta Prep 4000 Prep. Chrom. System
Waters 4000 System Controller
Waters 486 Tunable Absorbance Detector
Waters Fraction Collector
Merck Hitachi D-2000 Chromato-Integrator
Resin: LiChrospher 60 RP-select B, Merck No: 11023, 1 Kg
Flow: 65 ml/min. (Scaled up to 300×700 mm~2 L/min.)
λ: 230 nm
AUFS: 2 (detector sensitivity~lowest level)
A-buffer: 12% Ethanol (96%) in 0.10 M $CH_3COOH$ in Mili-Q-water.
Application sol.: Colistin base, 50 g~42 mmol (as is) is dissolved in 1000 ml 24% Ethanol (96%) by addition of 5.83 acid equivalents of $CH_3COOH$~245 mmol~14.5 ml 100% $CH_3COOH$ (17M); pH is adjusted with 2 M NaOH to pH=7.5; solution is membrane filtered (0.45) with use of Celite as filter aid
Ion strength: 4-6 mS/cm.

1) Equilibration of column: Equilibrated with A-buffer
2) Application: The colistin acetate solution (48 mg/ml) is applied at 65 ml/min during 14 min., followed by A-buffer during 0.1 min.~43.5 g applied
3) Elution: The column is eluted with A-buffer until absorption has dropped to the asymptote 0.010 V±10 mV and effluent is collected in 18 fractions of 3 min.~585 ml
4) Wash of column: 200 ml (4 min. at 50 ml/min) of a mixture of 24% ethanol and 50% 1.2 propanediol is applied, followed by A-buffer until absorption has decreased to zero level
5) HPLC analysis: Samples are diluted until area of $E_1$ reaches $20\text{-}30 \times 10^6$ AU (5×); high colistin standard typically reaches $20 \times 10^6$ AU; samples are analyzed by use of Colistin NovaS (30 min. run).

Example 3

Total Purification and Final Handling; Large Scale

Colistin sulfate mono-component (polymyxin $E_1$) is a fermentation product, which implies that its first appearance is in a fermented broth. Polymyxin $E_1$ is recovered and purified from the broth which contains a large variety of impurities and only a few grams of polymyxin $E_1$ and related substances per liter.

The recovery from the fermentation broth comprises precipitation of colistin (polymyxin $E_1$) and related substances and a primary separation by centrifugation. The secondary purification consists of reverse phase chromatography and precipitation, resulting in the more pure product with regards to polymyxin $E_1$. The related substances and impurities present in the colistin sulfate mono-component product are mainly co-fermented substances.

During fermentation of colistin a complex mixture of structurally related components is generated, with a ratio characteristic of each *Bacillus polymyxa* strain. Examples are:

Changes in the fatty acid chain, generating for instance either polymyxin $E_1$ (with 6-methyl octanoic acid) or polymyxin $E_2$ (with 7-methyl octanoic acid),
Replacement of amino acids in the molecule, for instance if D-Leucine in colistin is replaced by D-Phenylalanine, then the related antibiotic polymyxin B is generated. If L-Leucine in polymyxin $E_1$ is replaced with isoleucine, then polymyxin $E_1$-isoleucine is generated Purification by Preparative HPLC The following buffers are prepared:
Buffer I: 1.6-2 M ethanol and 0.1-0.15 M acetic acid. The buffer is filtered through a 0.45 μm filter just before use.
Buffer II: Approx. 6.8 M 1,2-propanediol, approx. 4 M ethanol and approx. 0.1 M acetic acid. The buffer is filtered through a 0.45 μm filter just before use.

The HPLC column (diameter 30 cm) with a volume of approx. 48 liter, is equilibrated with approx. 40 liter of Buffer I. The flow is 0.8-1.2 l/min. (Same flow is used for all HPLC steps). The column is regenerated with approx. 8 liter of Buffer II followed by approx. 50 liter Buffer I or until UV-signal is back to baseline.

A vacuum dried colistin base batch, 1000-1500 g, is weighed out and suspended in 20-30 liter 4 M ethanol. The suspension is dissolved by adding a 0.3 M acetic acid while stirring for 30 min. pH is adjusted to approx. 7.5 with sodium hydroxide and the solution is filtered through a membrane filter, 0.45 μm. The colistin acetate solution is passed through the HPLC column and binds to the resin. The HPLC column is eluted with approx. 160 liter of Buffer I. The effluent is collected in fractions. Fractions complying with a pre-set specification are collected, while the rest of the fractions are discarded. A batch with a purity of at least 92% with regards to polymyxin $E_1$ is pooled from the fractions. Concentration of polymyxin $E_1$ and removal of excess ethanol is performed by reverse osmosis. The pool is concentrated to approx. 50 g/l and thereafter dialysed with DI-water (approx. 8 volumes).

Purification by Hydrophobic Interaction Chromatography (HIC)

The following buffers are prepared:
Calibration buffer: Approx. 200 mM $(NH_4)_2SO_4$; pH is adjusted to approx. 7 with diluted ammonia
Elution buffer: Approx. 200 mM $(NH_4)_2SO_4$; pH is adjusted to approx. 3.7 with acetic acid The HIC column (diameter 35 cm) with a volume of approx. 90 liter, is equilibrated with 250 liter of the calibration buffer, flow approx. 1.7 l/min, followed by approx. 200 liter elution buffer, flow approx. 1.0 l/min.

The salt content in the colistin acetate solution from reverse osmosis is adjusted to approx. 200 mM by adding $(NH_4)_2SO_4$ and pH is adjusted to approx. 7 with diluted ammonia. The concentration of the colistin acetate solution is 15-20 g/l. The solution is passed through the HIC column, flow 950-1050 ml/min. Elution proceeds with 10 times bed volume. Collection of effluent fractions is made automatically by PLC. Samples are drawn from each fraction and analyzed. Fractions complying with pre-set specifications are pooled, yielding a batch with a purity of 94-98% with regards to polymyxin $E_1$. Concentration of polymyxin $E_1$ and removal of ammonium sulphate is performed by ultra filtration to a concentration of 10-20 g/l.

Precipitation of Colistin Base Mono-Component

The solution is diluted to 10 g/l with DI-water and stirred until it is homogenous. pH is adjusted to 9.6-9.8 with sodium hydroxide, and stirring continues while colistin base mono-component precipitates. The precipitate is recovered by filtration on a filter press. When the filtration is completed, the cake is washed with approx. 800 liter of DI-water, which is displaced by air. The colistin mono-component cake is removed from the filter press and stored in the freezer.

Conversion to Colistin Sulfate Mono-Component

Colistin base mono-component is suspended and dissolved in DI-water while stirring. pH is adjusted to 5.0 with dilute sulphuric acid. The solution is filtered through 0.45 µm filter.

Lyophilisation, Milling and Storage

The filtered solution is filled into stainless steel freeze drying trays and lyophilized for about 70 hours using a PIC controlled temperature profile in the range −25° C.→+45° C. The dry product is removed from the lyophilizer and milled to obtain the desired particle distribution.

ANALYTICAL HPLC METHODS

Method 1: HPLC for In-Process Control from Fermentation to Colistin Base
Equipment: Waters automatic HPLC equipment, consisting of:
  Pump: Model 6000 A/510
  Injector: WISP 712 A
  Detector: Model 441
  Pre-filter: Guard Pak, Resolve C18 (may be omitted)
  Column: Resolve C18, 10×8.5 micron or Nova-Pak, 4 micron
  Column fitting: RCM 8×10
Method: Isocratic
  Mobile Phase:
  Buffer: Sodium sulfate decahydrate, 16.1 g (0.05 M) conc. acetic acid, 0.56 ml (0.01 M) triethylamine 20 ml (0.15 M), water to 1000 ml. pH adjusted to 2.5 with phosphoric acid.
  Alternative buffer: Sodium sulfate 0.04 M, methanesulfonic acid 0.56 M, triethylamine 0.087 M, pH to 3.0.
  Before use, acetonitrile, 170 g, is dissolved in the buffer to make 1000 ml.
  The solution is de-aerated with helium for 15 min.
Assay Procedure:
  Flow: 1.5 ml/min, alternative 1.0 ml/min.
  Temperature: Ambient.
  Injection volume: 20 micro-L, alternative 25.
  Detection: 214 nm, 0.1 AUFS or 1.0 AUFS.
  Running time: 30 min.
  Standard: Authentic standard of colistin sulfate, dissolved in water to make 1 mg/ml.
Standard: Colistin base, 1.0 mg/ml in 0.1 M hydrochloric acid.
Analytical samples: Diluted to contain 0.5-1 mg/ml. Diluent: 3% phosphoric acid, 40 ml, and acetonitrile, 60 ml. Centrifugation if turbid.

Method 2: HPLC for Colistin Base to Final Bulk Product
Equipment: Waters automatic HPLC equipment, consisting of:
  Pump: Model 510
  Injector: 717 plus auto sampler
  Detector: 490 E
  Pre-filter: Guard Pak, Nova-Pak, C18
  Column: Nova-Pak, C18, 60 Å, 4 µm, 150×4.6 mm.
  Column oven: Jones Chromatography Model 7955
Reagents:
  Sodium sulfate, water free, pro analysis
  Triethylamine, HPLC grade
  Methane sulphonic acid, ≥99%
  Milli-Q water
  Buffer: Sodium sulfate, water free, 28.4 g (0.10 M), triethylamine 14.0 ml (0.05 M), methanesulfonic acid 10.0 ml (0.06 M), Milli-Q water to 2000 ml.
The buffer is vacuum filtered through a 0.45 µm filter.
  A-eluent: 50% buffer, 35% Milli-Q water, 15% acetonitrile. Adjusted to pH 2.0 with methanesulfonic acid.
  B-eluent: 50% buffer, 20% Milli-Q water, 30% acetonitrile. Adjusted to pH 2.0 with methanesulfonic acid.
Sample Preparation:
  Colistin acetate: 1-2 g/l in 0.05 M acetic acid. Stirred for 30 minutes and filtered through a 0.45 µm membrane filter
Standards:
  Two in-house standards prepared, one with high activity (2000 µg/mg) and one with low activity (400 µg/mg).
Assay Procedure:
  Flow: 0.8 ml/min
  Temperature of column: 25° C.
  Detection: 214 nm
  Time constant: 1.0 sec.
  AUFS: 1.000 AU
  Auto zero: On
  Wisp temperature: 25° C.
  Injection: 20 µl/run
Gradient Program:

| Gradient | Time | Flow (ml/min) | % A | % B | % C | Curve |
|---|---|---|---|---|---|---|
| 1 | 0.00 | 0.8 | 67.0 | 33.0 | 0.0 | 0 |
| 2 | 15.00 | 0.8 | 67.0 | 33.0 | 0.0 | 6 |
| 3 | 25.00 | 0.8 | 30.0 | 70.0 | 0.0 | 6 |
| 4 | 30.00 | 0.8 | 30.0 | 70.0 | 0.0 | 6 |
| 5 | 31.00 | 0.8 | 67.0 | 33.0 | 0.0 | 6 |
| 6 | 40.00 | 0.8 | 67.0 | 33.0 | 0.0 | 6 |
| 7 | 41.00 | 0.8 | 0.0 | 100.0 | 0.0 | 6 |
| 8 | 50.00 | 0.8 | 0.0 | 100.0 | 0.0 | 6 |
| 9 | 51.00 | 0.00 | 0.0 | 100.0 | 0.0 | 6 |

Changes after 40 minutes are not part of the assay, are only performed after a series of analyses Eluent A is used as blind and subtracted from standards and samples.

Method 3: HPLC for Colistin Sulfate Mono-Component
Equipment: Waters automatic HPLC equipment, consisting of:
  Pump: Model 510
  Injector: 717 plus autosampler
  Detector: 490 E
  Column: Nova-Pak, C18, 60 Å, 4 µm, 250×4.6 mm
  Column oven: Jones Chromatography Model 7955
Reagents:
  Milli-Q water
  Acetonitrile, HPLC grade
  Methane sulfonic acid, ≥99%
  Triethylamine, HPLC grade
  Sodium sulfate, water free, pro analysis
  Buffer: Sodium sulfate, water free, 28.4 g (0.10 M), triethylamine 14.0 ml (0.05 M), methane sulfonic acid 10.0 ml (0.06 M), Milli-Q water to 2000 ml.

The buffer is vacuum filtered through a 0.45 µm filter.

A-eluent: 50% buffer, 35% Milli-Q water, 15% acetonitrile. Adjusted to pH 2.0 with methanesulfonic acid.

B-eluent: 50% buffer, 20% Milli-Q water, 30% acetonitrile. Adjusted to pH 2.0 with methanesulfonic acid.

Sample Preparation:

Colistin sulfate mono-component: 2.8 mg/ml in Milli-Q water. Stirred for 15 minutes. and filtered through a 0.45 µm filter.

Assay Procedure

Flow rate: 1.0 ml/min

Detection wavelength: 214 nm

Column temperature: 25° C.

Injection volume: 40 µl

Autosampler temperature: 25° C.

Gradient Program:

| Gradient | Time | Flow (ml/min) | % A | % B | Curve |
|---|---|---|---|---|---|
| 1 | 0.00 | 1.00 | 67.0 | 33.0 | 0 |
| 2 | 20.00 | 1.00 | 67.0 | 33.0 | 6 |
| 3 | 40.00 | 1.00 | 40.0 | 60.0 | 6 |
| 4 | 50.00 | 1.00 | 40.0 | 60.0 | 6 |
| 5 | 51.00 | 1.00 | 0 | 100.0 | 6 |
| 6 | 55.00 | 1.00 | 0 | 100.0 | 6 |
| 7 | 56.00 | 1.00 | 67.0 | 33.0 | 6 |
| 8 | 70.00 | 1.00 | 67.0 | 33.0 | 6 |
| 9 | 71.00 | 1.00 | 0 | 100 | 6 |
| 10 | 81.00 | 1.00 | 0 | 100 | 6 |
| 11 | 82.00 | 0 | 0 | 100 | 6 |

Changes after 70 minutes are not part of the assay, are only performed after a series of analyses

REFERENCES

1) Suzuki, T., Hayashi, K., Fujikawa, K. (1963) Studies on the Chemical Structure of Colistin: III. Enzymatic Hydrolysis of Colistin A, J Biochem 54: 412-418.

2) Elverdam, I., P. Larsen and E. Lund (1981) Isolation and characterization of three new polymyxins in polymyxin B and E by high-performance liquid chromatography. J. Chrom. (218) 653-661

The invention claimed is:

1. A method for purification of colistin by reverse phase chromatography, comprising
   loading a column with colistin base in acetic acid and a high ethanol concentration of greater than or equal to 20% by volume
   and
   eluting the colistin with a low ethanol concentration of less than 20% by volume.

2. The method according to claim 1, wherein the high ethanol concentration is 20%-30% by volume.

3. The method according to claim 1, wherein the high ethanol concentration is 20%-24% by volume.

4. The method according to claim 1, wherein the high ethanol concentration is 24% by volume.

5. The method according to claim 1, wherein the low ethanol concentration is 10-15% by volume.

6. The method according to claim 1, wherein the low ethanol concentration is 12% by volume.

7. The method according to claim 1, wherein the acetic acid concentration is 0.1 M.

8. The method according to claim 1, further comprising a step of Hydrophobic interaction chromatography following eluting the colistin with a low ethanol concentration.

9. The method according to claim 1, wherein the pH of the mobile phase is 7-8.

10. The method according to claim 1, wherein the pH of the mobile phase is 7.5.

11. The method according to claim 1, wherein
    the high ethanol concentration is 24%,
    the low ethanol concentration is 12%,
    the acetic acid concentration is 0.1 M,
    the pH of the mobile phase is 7.5, and
    the stationary phase is a C8-resin.

\* \* \* \* \*